United States Patent
Santmyer et al.

(10) Patent No.: US 8,701,931 B2
(45) Date of Patent: Apr. 22, 2014

(54) MEDICATION DISPENSING CABINET AND ASSOCIATED DRAWER ASSEMBLY HAVING POCKETS WITH CONTROLLABLY OPENABLE LIDS

(75) Inventors: Paul Santmyer, Canonsburg, PA (US); Todd Kijowski, Natrona Heights, PA (US); Ben Tylenda, Venetia, PA (US); Pat Braun, Pittsburgh, PA (US)

(73) Assignee: Aesynt Incorporated, Cranberry, PA (US)

( * ) Notice: Subject to any disclaimer, the term of this patent is extended or adjusted under 35 U.S.C. 154(b) by 471 days.

(21) Appl. No.: 13/075,433

(22) Filed: Mar. 30, 2011

(65) Prior Publication Data

US 2012/0248134 A1    Oct. 4, 2012

(51) Int. Cl.
- *B65G 59/00*    (2006.01)
- *G06F 17/00*    (2006.01)
- *E06B 3/50*    (2006.01)
- *E05C 7/06*    (2006.01)

(52) U.S. Cl.
USPC ...... 221/92; 221/4; 221/1; 221/154; 700/237; 700/231; 700/242; 312/218; 312/328; 312/209; 312/109; 312/222; 312/215

(58) Field of Classification Search
CPC .......... B65G 59/00; G06F 17/00; E06B 3/50; E05C 7/06
USPC ................. 312/218, 328, 209, 109, 222, 215; 221/1, 92, 154, 4; 700/237, 231, 242
See application file for complete search history.

(56) References Cited

U.S. PATENT DOCUMENTS

| 4,717,042 A | 1/1988 | McLaughlin |
| 4,785,969 A | 11/1988 | McLaughlin |

(Continued)

FOREIGN PATENT DOCUMENTS

| WO | WO 99/30248 A1 | 6/1999 |
| WO | WO 9960982 A2 * | 12/1999 |
| WO | WO 2009/153756 A1 | 12/2009 |

OTHER PUBLICATIONS

Ezy-Dose 7 Day AM/PM Push Button Pill Reminder [online] [retrieved Feb. 18, 2011]. Retrieved from the Internet: <URL: http://www.medichest.com/ezy-dose7dayampmpushbuttonpillreminderea.html>. 1 page.

(Continued)

*Primary Examiner* — Gene Crawford
*Assistant Examiner* — Rakesh Kumar
(74) *Attorney, Agent, or Firm* — Alston & Bird LLP (57) ABSTRACT

A medication dispensing cabinet, a medication dispensing drawer assembly and an associated method are provided to facilitate controlled access to medications in an efficient manner. A medication dispensing cabinet includes a cabinet body, a plurality of drawers disposed within and configured for slidable extension relative to the cabinet body and a plurality of pockets serially positioned within a drawer. Each pocket includes a lid configured to cover the pocket and limit access to medication within the pocket. The medication dispensing cabinet also includes a linkage member configured to operably engage the lids of the plurality of pockets. The linkage member has a first state in which the linkage member prevents one or more of the lids from being opened and a second state in which the linkage member permits the lids to be opened in accordance with a predefined sequential order.

20 Claims, 9 Drawing Sheets

(56) References Cited

U.S. PATENT DOCUMENTS

| | | | |
|---|---|---|---|
| 4,813,753 A * | 3/1989 | Relyea | 312/291 |
| 4,847,764 A | 7/1989 | Halvorson | |
| 5,014,875 A | 5/1991 | McLaughlin et al. | |
| 5,190,185 A | 3/1993 | Blechl | |
| 5,292,029 A | 3/1994 | Pearson | |
| 5,314,243 A | 5/1994 | McDonald et al. | |
| 5,346,297 A | 9/1994 | Colson, Jr. et al. | |
| 5,377,864 A | 1/1995 | Blechl et al. | |
| 5,405,048 A | 4/1995 | Rogers et al. | |
| 5,431,299 A | 7/1995 | Brewer et al. | |
| 5,460,294 A | 10/1995 | Williams | |
| 5,468,110 A | 11/1995 | McDonald et al. | |
| 5,480,062 A | 1/1996 | Rogers et al. | |
| 5,520,450 A | 5/1996 | Colson, Jr. et al. | |
| 5,564,803 A | 10/1996 | McDonald et al. | |
| 5,593,267 A | 1/1997 | McDonald et al. | |
| 5,661,978 A | 9/1997 | Holmes et al. | |
| D384,578 S | 10/1997 | Wangu et al. | |
| 5,713,485 A | 2/1998 | Liff et al. | |
| 5,716,114 A | 2/1998 | Holmes et al. | |
| 5,745,366 A | 4/1998 | Higham et al. | |
| 5,761,877 A | 6/1998 | Quandt | |
| 5,797,515 A | 8/1998 | Liff et al. | |
| 5,805,456 A | 9/1998 | Higham et al. | |
| 5,842,976 A | 12/1998 | Williamson | |
| 5,878,885 A | 3/1999 | Wangu et al. | |
| 5,880,443 A | 3/1999 | McDonald et al. | |
| 5,883,806 A | 3/1999 | Meador et al. | |
| 5,893,697 A | 4/1999 | Zini et al. | |
| 5,905,653 A | 5/1999 | Higham et al. | |
| 5,912,818 A | 6/1999 | McGrady et al. | |
| 5,927,540 A | 7/1999 | Godlewski | |
| 5,940,306 A | 8/1999 | Gardner et al. | |
| 5,971,593 A | 10/1999 | McGrady | |
| 6,000,546 A * | 12/1999 | Noble | 206/538 |
| 6,003,006 A | 12/1999 | Colella et al. | |
| 6,011,999 A * | 1/2000 | Holmes | 700/231 |
| 6,021,392 A | 2/2000 | Lester et al. | |
| 6,039,467 A | 3/2000 | Holmes | |
| 6,065,819 A | 5/2000 | Holmes et al. | |
| 6,068,156 A | 5/2000 | Liff et al. | |
| 6,109,774 A | 8/2000 | Holmes et al. | |
| 6,112,502 A | 9/2000 | Frederick et al. | |
| 6,116,461 A * | 9/2000 | Broadfield et al. | 221/98 |
| 6,151,536 A | 11/2000 | Arnold et al. | |
| 6,169,707 B1 * | 1/2001 | Newland | 368/10 |
| 6,170,230 B1 | 1/2001 | Chudy et al. | |
| 6,176,392 B1 | 1/2001 | William et al. | |
| 6,189,727 B1 | 2/2001 | Shoenfeld | |
| 6,223,934 B1 | 5/2001 | Shoenfeld | |
| 6,256,967 B1 | 7/2001 | Hebron et al. | |
| 6,283,322 B1 | 9/2001 | Liff et al. | |
| 6,289,656 B1 | 9/2001 | Wangu et al. | |
| 6,338,007 B1 | 1/2002 | Broadfield et al. | |
| 6,339,732 B1 | 1/2002 | Phoon et al. | |
| 6,361,263 B1 | 3/2002 | Dewey et al. | |
| 6,370,841 B1 | 4/2002 | Chudy et al. | |
| 6,449,927 B2 | 9/2002 | Hebron et al. | |
| 6,471,089 B2 | 10/2002 | Liff et al. | |
| 6,497,342 B2 | 12/2002 | Zhang et al. | |
| 6,499,270 B2 | 12/2002 | Peroni et al. | |
| 6,532,399 B2 | 3/2003 | Mase | |
| 6,550,618 B2 * | 4/2003 | Peterson | 206/534 |
| 6,564,121 B1 | 5/2003 | Wallace et al. | |
| 6,581,798 B2 | 6/2003 | Liff et al. | |
| 6,609,047 B1 | 8/2003 | Lipps | |
| 6,611,733 B1 | 8/2003 | De La Huerga | |
| 6,625,952 B1 | 9/2003 | Chudy et al. | |
| 6,631,805 B2 * | 10/2003 | Bramen | 206/538 |
| 6,640,159 B2 | 10/2003 | Holmes et al. | |
| 6,650,964 B2 | 11/2003 | Spano, Jr. et al. | |
| 6,671,579 B2 | 12/2003 | Spano, Jr. et al. | |
| 6,681,149 B2 | 1/2004 | William et al. | |
| 6,742,671 B2 | 6/2004 | Hebron et al. | |
| 6,755,931 B2 | 6/2004 | Vollm et al. | |
| 6,760,643 B2 | 7/2004 | Lipps | |
| 6,776,304 B2 | 8/2004 | Liff et al. | |
| 6,785,589 B2 | 8/2004 | Eggenberger et al. | |
| 6,790,198 B1 | 9/2004 | White et al. | |
| 6,814,254 B2 | 11/2004 | Liff et al. | |
| 6,814,255 B2 | 11/2004 | Liff et al. | |
| 6,847,861 B2 | 1/2005 | Lunak et al. | |
| 6,874,684 B1 | 4/2005 | Denenberg et al. | |
| 6,883,680 B2 * | 4/2005 | Hirose | 220/830 |
| 6,892,780 B2 | 5/2005 | Vollm et al. | |
| 6,895,304 B2 | 5/2005 | Spano, Jr. et al. | |
| 6,975,922 B2 | 12/2005 | Duncan et al. | |
| 6,985,797 B2 | 1/2006 | Spano, Jr. et al. | |
| 6,996,455 B2 | 2/2006 | Eggenberger et al. | |
| 7,010,389 B2 | 3/2006 | Lunak et al. | |
| 7,014,063 B2 | 3/2006 | Shows et al. | |
| 7,016,766 B2 | 3/2006 | William et al. | |
| 7,040,504 B2 | 5/2006 | Broadfield et al. | |
| 7,052,097 B2 * | 5/2006 | Meek et al. | 312/222 |
| 7,072,737 B2 | 7/2006 | Lunak et al. | |
| 7,072,855 B1 | 7/2006 | Godlewski et al. | |
| 7,077,286 B2 | 7/2006 | Shows et al. | |
| 7,085,621 B2 | 8/2006 | Spano, Jr. et al. | |
| 7,092,796 B2 | 8/2006 | Vanderveen | |
| 7,093,755 B2 | 8/2006 | Jordan et al. | |
| 7,100,792 B2 | 9/2006 | Hunter et al. | |
| 7,103,419 B2 | 9/2006 | Engleson et al. | |
| 7,111,780 B2 | 9/2006 | Broussard et al. | |
| 7,139,639 B2 | 11/2006 | Broussard et al. | |
| 7,142,944 B2 * | 11/2006 | Holmes et al. | 700/237 |
| 7,150,724 B2 | 12/2006 | Morris et al. | |
| 7,171,277 B2 | 1/2007 | Engleson et al. | |
| 7,218,231 B2 | 5/2007 | Higham | |
| 7,228,198 B2 | 6/2007 | Vollm et al. | |
| 7,249,688 B2 | 7/2007 | Hunter et al. | |
| 7,348,884 B2 | 3/2008 | Higham | |
| 7,417,729 B2 | 8/2008 | Greenwald | |
| 7,419,133 B2 | 9/2008 | Clarke et al. | |
| 7,426,425 B2 | 9/2008 | Meek, Jr. et al. | |
| 7,554,449 B2 | 6/2009 | Higham | |
| 7,571,024 B2 | 8/2009 | Duncan et al. | |
| 7,588,167 B2 | 9/2009 | Hunter et al. | |
| 7,748,554 B2 * | 7/2010 | Murphy | 220/23.4 |
| 7,909,418 B2 * | 3/2011 | McFarland | 312/215 |
| 8,090,473 B2 * | 1/2012 | Higham | 700/242 |
| 8,193,918 B1 * | 6/2012 | Shavelsky et al. | 340/309.16 |
| 8,197,017 B2 * | 6/2012 | Rahilly | 312/222 |
| 8,234,008 B2 * | 7/2012 | Weber | 700/242 |
| 8,262,174 B2 * | 9/2012 | Rahilly | 312/109 |
| 8,317,027 B2 * | 11/2012 | Pabari et al. | 206/532 |
| 8,332,066 B2 * | 12/2012 | Weber | 700/242 |
| 8,335,588 B2 * | 12/2012 | Rahilly et al. | 700/242 |
| 8,457,784 B2 * | 6/2013 | Rahilly et al. | 700/242 |
| 8,517,215 B2 * | 8/2013 | Shafir | 221/152 |
| 2004/0056651 A1 * | 3/2004 | Marietta Bersana | 324/207.2 |
| 2009/0114562 A1 * | 5/2009 | Noble et al. | 206/538 |
| 2010/0219198 A1 * | 9/2010 | Goldman | 221/25 |

OTHER PUBLICATIONS

Amazon.com: Apex Weekly Pill Organizer, Twice-a-Day, 1 Pill Organizer (Colors May . . . [online] [retrieved Feb. 18, 2011]. Retrieved from the Internet: <URL: http://www.amazon.com/Apex-Weekly-Organizer-Twice-Colors/dp/B000EGKTEW>. 6 pages.

Office Action for Canadian Application No. 2,772,899 dated May 13, 2013.

* cited by examiner

MEDICATION DISPENSING CABINET AND ASSOCIATED DRAWER ASSEMBLY HAVING POCKETS WITH CONTROLLABLY OPENABLE LIDS

TECHNOLOGICAL FIELD

Embodiments of the present invention relate generally to medication dispensing cabinets and associated drawer assemblies and, more particularly, to medication dispensing cabinets and associated drawer assemblies having a plurality of pockets with controllably openable lids.

BACKGROUND

Medication dispensing cabinets have been developed in order to store and controllably dispense a variety of medications. A medication dispensing cabinet may include a cabinet body with one or more drawers that are slidably disposed within the cabinet body. The drawers store the various medications or medical supplies. While some of the drawers may be unlatched and freely openable, other drawers may be locked in order to more closely control access to the medication stored in the locked drawers.

Some medication dispensing cabinets are automated and, as such, include or are otherwise associated with a computer that controls access to the medications stored within the cabinet. The computer may allow access to only authorized users, such as medical providers who work in the unit in which the medication dispensing cabinet is located. Once authorized by the computer, a medical provider may identify a particular medication to be dispensed, such as by reference to the medication prescribed to a respective patient to whom the medical provider is attending. The computer may then unlock the respective drawer in which the particular medication is stored so as so provide access to the medication.

Even when unlocked, some drawers may be configured to controllably limit the contents of the drawer that may be accessed by the medical provider. For example, a drawer may include a series of pockets or storage locations arranged in a linear fashion, from the front to the rear of the cabinet. Each pocket may include a predefined quantity of medication, such as a single dose or unit dose of a medication. In order to control access to the medication within the pockets, each pocket may include a lid that must be opened in order to access the medication therein. Some drawers have lids that are locked so as to prevent unauthorized access to the medication within the respective pockets. As with a locked drawer, a computer of an automated medication dispensing cabinet may only allow access to the medication within a respective pocket by unlocking the lid for authorized users who have identified a need for the medication within the respective pocket. In this regard, once a user has been authorized by the computer and the particular medication to be dispensed has been identified, such as by reference to the medications prescribed to a patient for whom the medical provider is attending, the computer may not only unlock the drawer in which the medication is stored, but may also unlock the lid of the pocket in which the medication is stored. As such, the medical provider may retrieve the medication from the pocket having the unlocked lid, but may not access the medication within the other pockets within the drawer, even though the drawer itself is unlocked.

Thus, a medication dispensing cabinet having a controllably locked lidded pocket may provide further control over the access to medications therein. Notwithstanding the level of control provided by controllably locked, lidded pockets, it may be desirable for medication dispensing cabinets and associated drawer assemblies to be further improved in order to facilitate the controlled access to the medication stored therein, as well as the other functions of a medication dispensing cabinet.

BRIEF SUMMARY

A medication dispensing cabinet, a medication dispensing drawer assembly and an associated method are provided in accordance with embodiments of the present invention to provide for improvements in the controlled access to medications stored within a medication dispensing cabinet. For example, the medication dispensing cabinet, medication dispensing drawer assembly and associated method of one embodiment may control access to medications, but, if authorized, may provide for quick and efficient access to the medications. The medication dispensing cabinet, medication dispensing drawer assembly and associated method may also maintain an accurate count of the medications that have been dispensed and those that remain within the cabinet for inventory control and replenishment purposes.

In one embodiment, a medication dispensing cabinet is provided that includes a cabinet body, a plurality of drawers disposed within and configured for slidable extension relative to the cabinet body and a plurality of pockets serially positioned within a first drawer. Each pocket includes a lid configured to cover the pocket and limit access to medication within this pocket. The medication dispensing cabinet of this embodiment also includes a linkage member configured to operably engage the lids of the plurality of pockets. The linkage member of this embodiment has a first state in which the linkage member prevents one or more of the lids from being opened and a second state in which the linkage member permits a lid to be opened in accordance with a predefined sequential order.

The medication dispensing cabinet may also include a latch configured to engage the linkage member in the first state and to be disengaged from the linkage member in the second state. The medication dispensing cabinet may include a bias member configured to urge the linkage member into operable engagement with the lids of the plurality of pockets. The medication dispensing cabinet of one embodiment also includes a sensor configured to detect opening or closing of a lid. In this embodiment, the medication dispensing cabinet can further include one or more magnets carried by each lid with the sensor being configured to detect at least one magnet in an instance in which a respective lid is opened or closed.

Each lid of one embodiment may include an engagement member extending laterally therefrom. The linkage member of this embodiment may also include a plurality of engagement members spaced lengthwise therealong for operable engagement with the engagement member of the respective lids. The pockets may be positioned and the lids may be configured such that a first lid is prevented from fully opening as a result of operable contact with the lid of an adjacent pocket in an instance in which the lid of the adjacent pocket has not yet been opened. The lids of one embodiment may be configured to move between a closed position and an open position that are separated by 180°.

In another embodiment, a medication dispensing drawer assembly is provided that includes a drawer, a plurality of pockets serially positioned within the drawer and a linkage member extending alongside the plurality of pockets. Each pocket includes a lid configured to cover the pocket and limit access to medication within the pocket. The linkage member is configured to operably engage the lids of the plurality of pockets. The linkage member has a locked state in which the linkage member prevents one or more of the lids from being opened and an unlocked state in which the linkage member permits a lid to be opened in accordance with a predefined sequential order.

The medication dispensing drawer assembly may also include a latch configured to engage the linkage member in the locked state and to be disengaged from the linkage member in the unlocked state. A medication dispensing drawer assembly may include a bias member configured to urge the linkage member into operable engagement with the plurality of pockets. The medication dispensing drawer assembly may include a sensor configured to detect opening or closing of a lid. In this embodiment, the medication dispensing drawer assembly may also include one or more magnets carried by its lid with the sensor being configured to detect at least one of the magnets in an instance in which a respective lid is opened or closed.

Each lid of one embodiment may include an engagement member extending laterally therefrom. The linkage member of this embodiment may include a plurality of engagement members spaced lengthwise therealong for operable engagement with the engagement members of respective lids. The plurality of pockets may be positioned, and the lids may be configured such that a first lid is prevented from fully opening as a result of operable contact with the lid of an adjacent pocket in an instance in which the lid of the adjacent pocket has not yet been opened. The lids may be configured to move between a closed position and an opened position that are separated by 180°.

In a further embodiment, a method for controllably dispensing medication is provided that includes maintaining a linkage bar in a locked state in order to prevent one or more lids that cover respective pockets within a drawer from being opened. The method also includes unlocking the linkage bar and permitting a lid to be opened while the linkage bar is unlocked so as to prevent access to medication within the respective pocket. For example, the method of one embodiment may permit the lid to be opened by requiring the lids to be opened in a sequential fashion. The method of one embodiment may also sense the opening or closing of the lid. The method also relocks the linkage bar while the lid remains open.

BRIEF DESCRIPTION OF THE SEVERAL VIEWS OF THE DRAWINGS

Having thus described embodiments of the invention in general terms, reference will now be made to the accompanying drawings, which are not necessarily drawn to scale, and wherein:

DETAILED DESCRIPTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
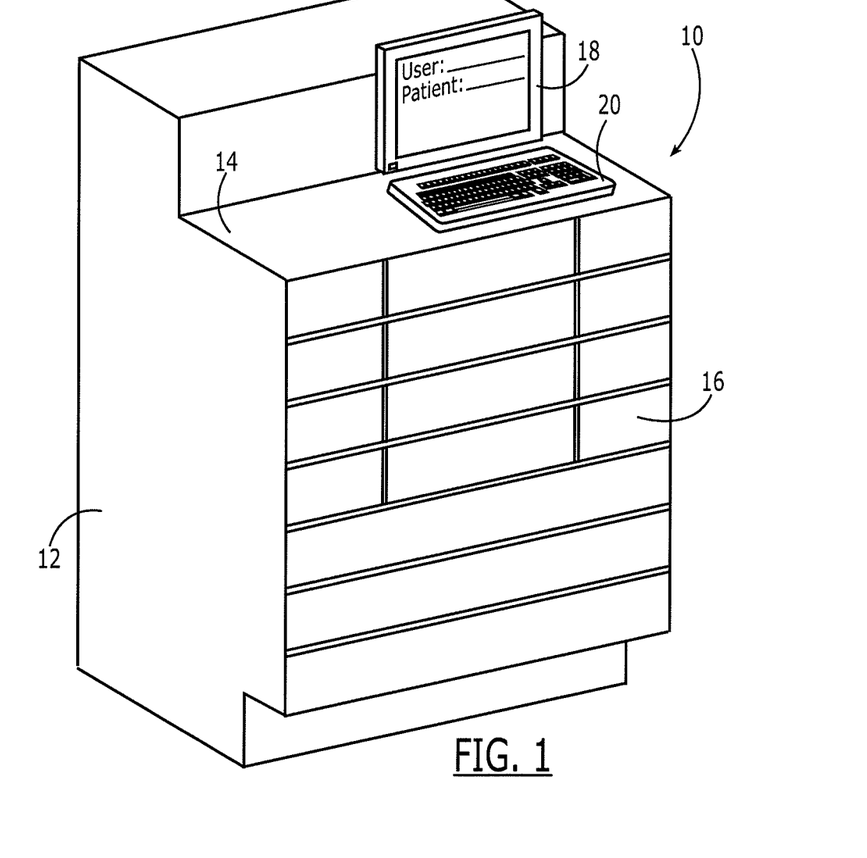
FIG. 1 is a perspective view of a medication dispensing cabinet in accordance with one embodiment of the present invention.

Referring now to FIG. 1, a cabinet 10 for storing a plurality of medication in accordance with one embodiment of the present invention is illustrated. As shown, the cabinet may include a cabinet body 12 having an upper work surface 14 and defining an internal cavity. The cabinet also includes one or more drawers 16 that are slidably disposed within the cabinet body, such as within the internal cavity defined by the cabinet body. The cabinet of one embodiment may be automated and, as such, may include a computer, such as a personal computer, work station or the like, for controlling access to medications stored by the cabinet. As shown in FIG. 1, the computer may be carried by the cabinet and may include a display 18, a keyboard 20, a processing unit (not shown) including or associated with a memory device, and the like. Alternatively, the computer or at least the processing unit may be remote from the cabinet body, but may be associated with and in communication with the cabinet body and the drawers so as to control access to the medications.

Figure 2:
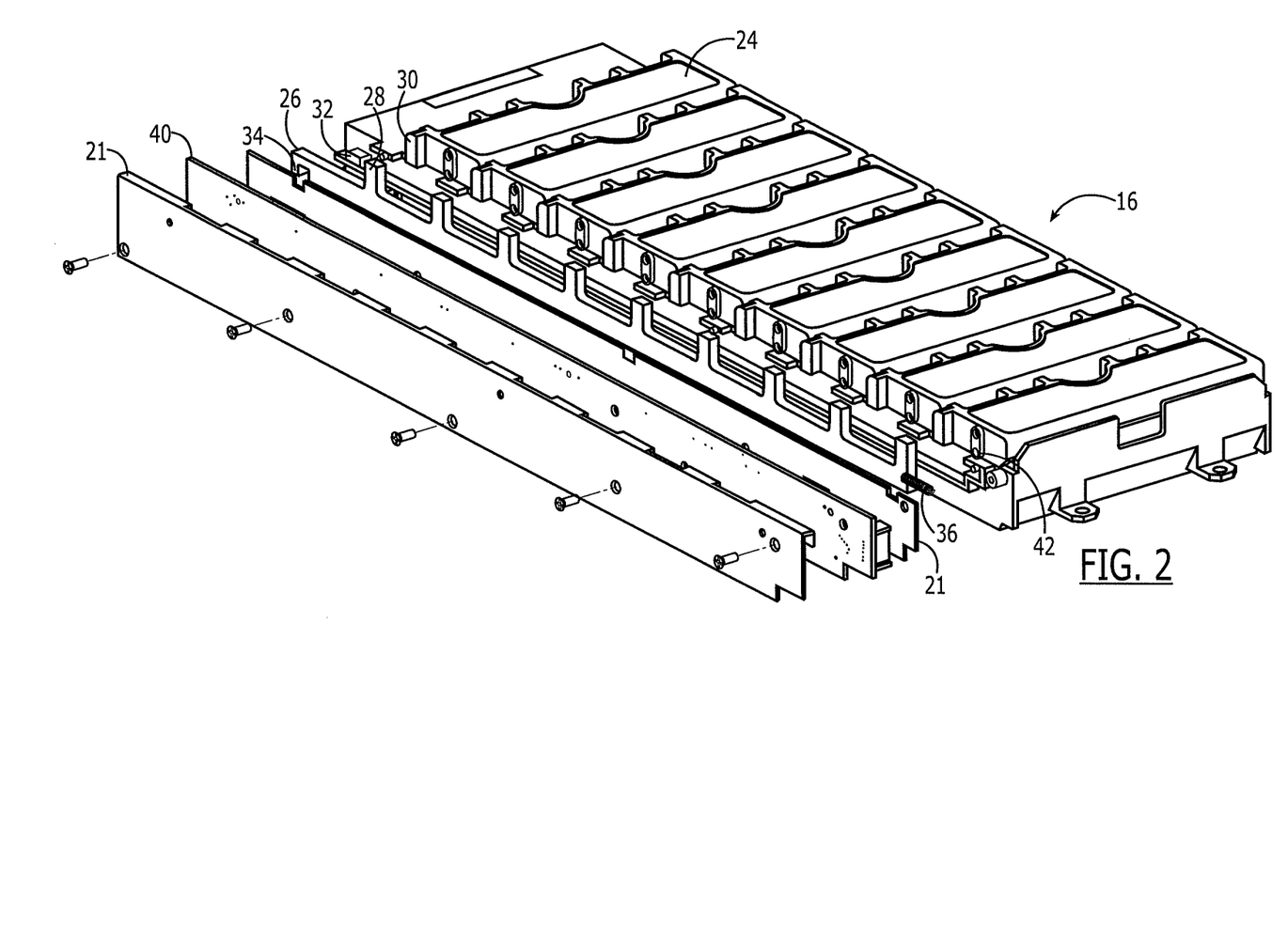
FIG. 2 is an exploded perspective view of a drawer assembly according to one embodiment of the present invention.

A drawer 16 may be slidably extended relative to the cabinet body 12. In an instance in which a drawer is lockable, the drawer must first be unlocked and may then be slidably extended relative to the cabinet body. In this regard, a drawer assembly in accordance with one embodiment of the present invention is illustrated in FIG. 2, albeit in an exploded view with several side panels 21 or other components removed so as to illustrate the drawer as well as the other constituent parts of a drawer assembly of one embodiment. The drawer assembly includes the drawer and a plurality of pockets 22 disposed within the drawer that are storage locations for the medication. While different medications may be stored in the different pockets, the drawer assembly of one embodiment stores the same medication within each of the pockets. While the quantity of the medication stored in each pocket may vary, the drawer assembly of one embodiment stores the same quantity of the same medication in each pocket, such as a unit or a single dose of the medication. In this regard, a pocket may contain a bottle or other container for containing the medication. Alternatively, the medication may be disposed in the pockets in other manners, such as by placing tablets, pills or the like within the pocket.

The drawer assembly also includes a plurality of lids 24, one of which is associated with and covers a respective pocket 22. As described below, the lids may be hinged so as to move between a closed position as shown in FIG. 2 in which the lid prevents access to the mediation within a respective pocket and an open position in which the pocket is exposed such that a medical provider may access the medications within the pocket. Between the opened and closed position, a lid may be rotated through a predefined angle, such as 180°. The lids may be formed of various materials, but in one embodiment are transparent or semi-transparent to permit a medical provider to view the contents of a pocket, even in an instance in which the lid is in a closed position. As such, the lids of this embodiment may be formed of a plastic or other resinous material.

The lids 24 may be locked in the closed position so as to prevent uncontrolled access to the medications within the pockets 22. However, a lid may be controllably unlocked in an instance in which the dispensing of medication from the respective pocket in the drawer 16 has been authorized. For example, the computer associated with a cabinet 10 may control the locking and unlocking of the lids so as to control the access to the medications within the pockets. The drawer assembly of one embodiment may be configured such that all of the lids are either locked or unlocked. However, even in an instance in which all of the lids are unlocked, the drawer assembly of the embodiment described below may include lids that are configured such that only a single lid may be opened at any one time. Indeed, the drawer assembly of this embodiment may be configured such that the lids are required to be opened in a sequential fashion, such as from the front to the back of the drawer.

In order to lock the plurality of lids 24, the drawer assembly may include a linkage member 26, such as a linkage bar, that extends alongside the plurality of pockets 22, such as lengthwise along the plurality of pockets from the front to the rear of the drawer 16. The linkage member is configured to operably engage the lids of the plurality of pockets. While the linkage member may engage the lids in a number of different manners, the linkage member of the illustrated embodiment includes a plurality of engagement members 28 spaced lengthwise therealong. For example, the engagement members of the linkage member may be upstanding posts spaced apart in a lengthwise direction with the spacing between the upstanding posts being equal to the spacing between the pockets in the drawer assembly. In this embodiment, the lids may also include corresponding engagement members 30 that extend laterally therefrom, such as the laterally extending members of the illustrated embodiment. The engagement members of the linkage member and the engagement members of the lid are positioned in a paired relationship with an engagement member of each pocket being adjacent to and in operable contact with a respective engagement member of the linkage member. In other words, the paired relationship of the engagement members of the linkage member and the engagement members of the lid results, for each pair, that the engagement members of the linkage member and the lid are in operable contact with one another.

Figure 3:
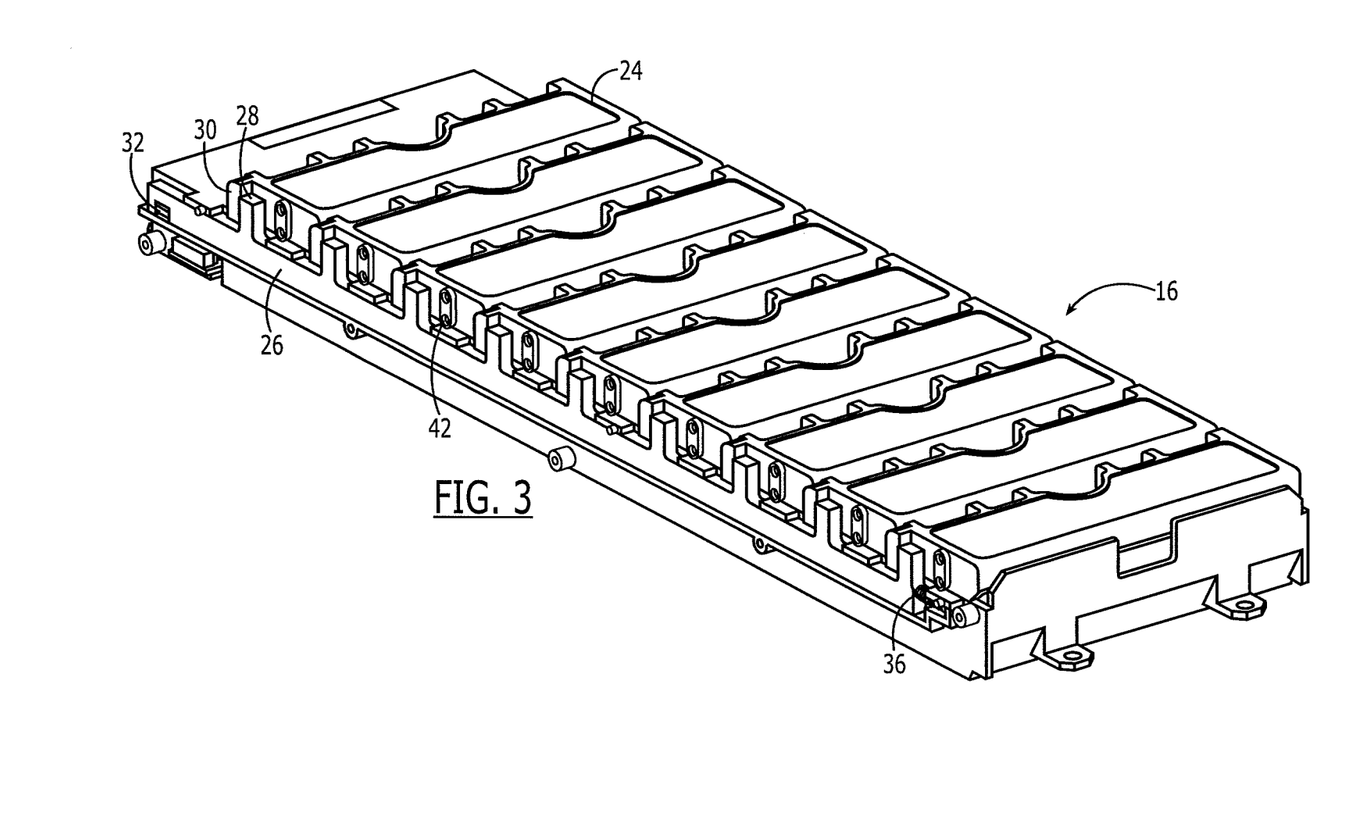
FIG. 3 is a perspective view of a portion of a drawer assembly according to one embodiment of the present invention in which each of the lids are closed.

In an instance in which the linkage member 26 is in a first state, such as a locked state, side surfaces of each pair of engagement members, that is, an engagement member 30 of a lid 24 and the corresponding engagement member 28 of the linkage member, may be adjacent to and in operable contact with one another. In the first state, such as the locked state, the linkage member is fixed in position relative to the plurality of pockets 22 such that the linkage member is unable to move in the lengthwise direction. Thus, the operable contact between the engagement members of the linkage member and the engagement members of the lids prevents the lids from rotating and, therefore, locks the lids in a fixed position, such as a closed position, as shown in FIG. 3.

Figure 3A:
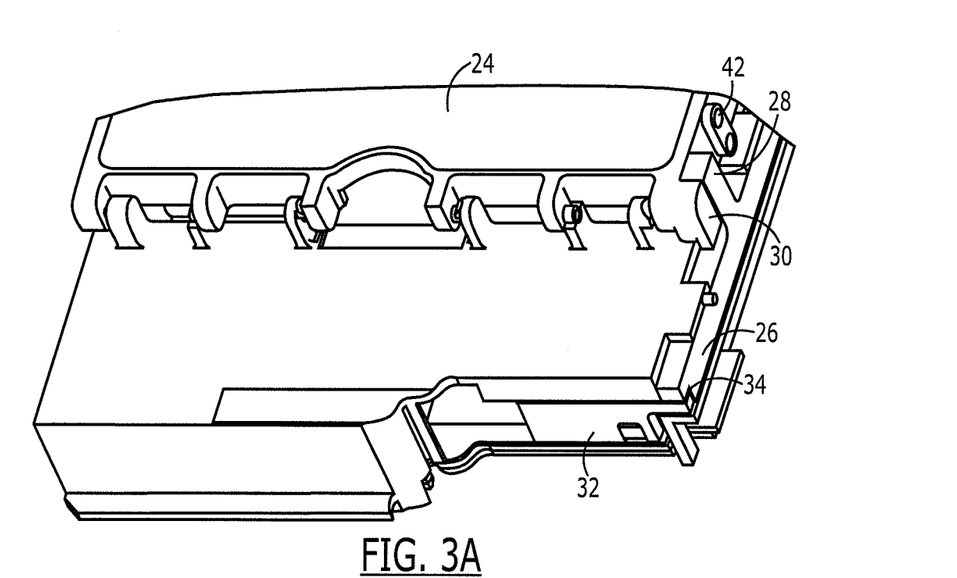
FIGS. 3A and 3B are fragmentary cross-sectional views of a portion of the drawer assembly according to one embodiment of the present invention which illustrate the latch in engaged and disengaged positions, respectively.
Figure 3B:
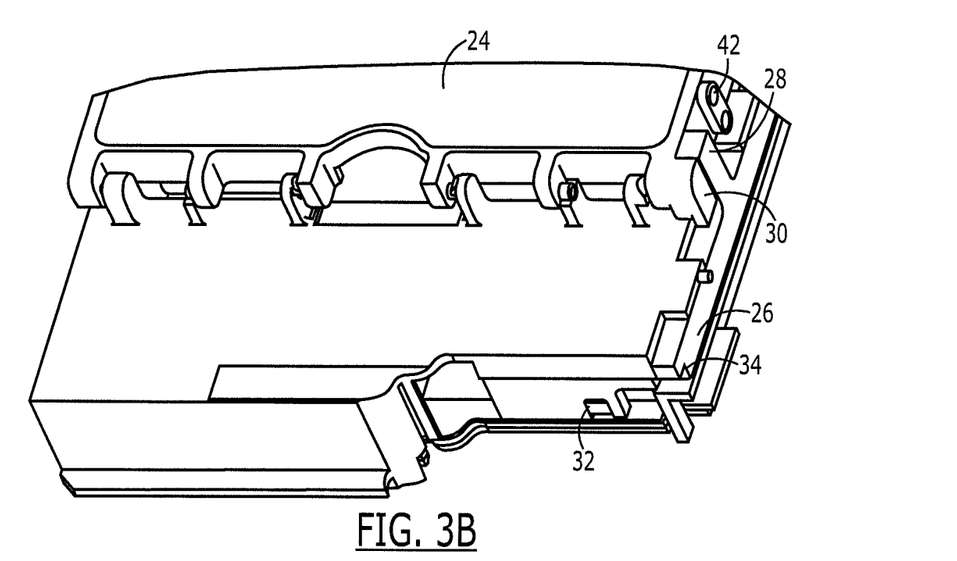

The drawer assembly may lock the linkage member 26 in position, such as in a first state, e.g., a locked state, in various manners. In the illustrated embodiment, however, the drawer assembly includes a latch 32 that is configured for lateral movement in a direction generally perpendicular to the lengthwise direction in which the linkage member extends. The latch may be controlled so as to move between a first position in which the latch engages the linkage member as shown in FIG. 3 and in fragmentary cross-section in FIG. 3A and a second position in which the latch is retracted and disengaged from the linkage member as shown in fragmentary cross-section in FIG. 3B. While the latch engages the linkage member, the linkage member is prevented from moving relative to the pockets 22. However, while the latch is disengaged from the linkage member, the linkage member is permitted to move in the lengthwise direction. Although the latch may engage the linkage member in a variety of different manners, the latch and linkage member of the illustrated embodiment are configured such that the linkage member defines a recess or cut-out 34 that is in alignment with the latch. As such, the latch of the illustrated embodiment may be positioned within the cut-out of the linkage member in an instance in which the linkage member is to be locked in position and may be retracted or otherwise removed from the cut-out so as to no longer engage the linkage member in the unlocked state so as to permit the linkage member to move in a lengthwise direction.

The latch 32 may be controlled, in one embodiment, by the computer of an automated medication dispensing cabinet 10. In this regard, the computer may controllably position the latch in either a locked or an unlocked position. The computer may control the position of the latch in various manners, such as by means of a DC motor and an associated linkage mechanism. The medication dispensing cabinet may also include a manual override feature. For example, the medication dispensing cabinet may include a hardware manual override assembly that permits a user to unlock all of the pockets 22 in a drawer assembly in the event of the loss of power. In this embodiment, the hardware manual override assembly may include a mechanical lock that may be unlocked or opened with a key to provide user access. Additionally or alternatively, the medication dispensing cabinet may include a software manual override to permit the user to unlock all of the pockets in a drawer assembly if the user wishes to bypass the normal workflow.

In an instance in which medication located within a pocket 22 is to be accessed, such as in response to an authorized user identifying medication to be dispensed, such as by reference to a prescription of a patient for whom the medical provider is attending, the computer may direct that the latch 32 be moved from a locked position to an unlocked position. Once unlocked, the linkage member 26 is capable of movement in a lengthwise direction relative to the plurality of serially positioned pockets. In the illustrated embodiment, however, the drawer assembly also includes a bias member 36, such as a spring, configured to urge the linkage member in a lengthwise direction relative to the plurality of pockets such that the engagement members 28 of the linkage member are urged into operable contact with the corresponding engagement members 30 of the lids 24. This operable contact between the engagement members of the lids and the linkage member that is maintained by the bias member even once the linkage member has been unlocked may prevent inadvertent opening of the lids by still requiring the application of an opening force intended to rotate a lid from the closed position to the open position in order to effect the opening of a lid.

Figure 4:
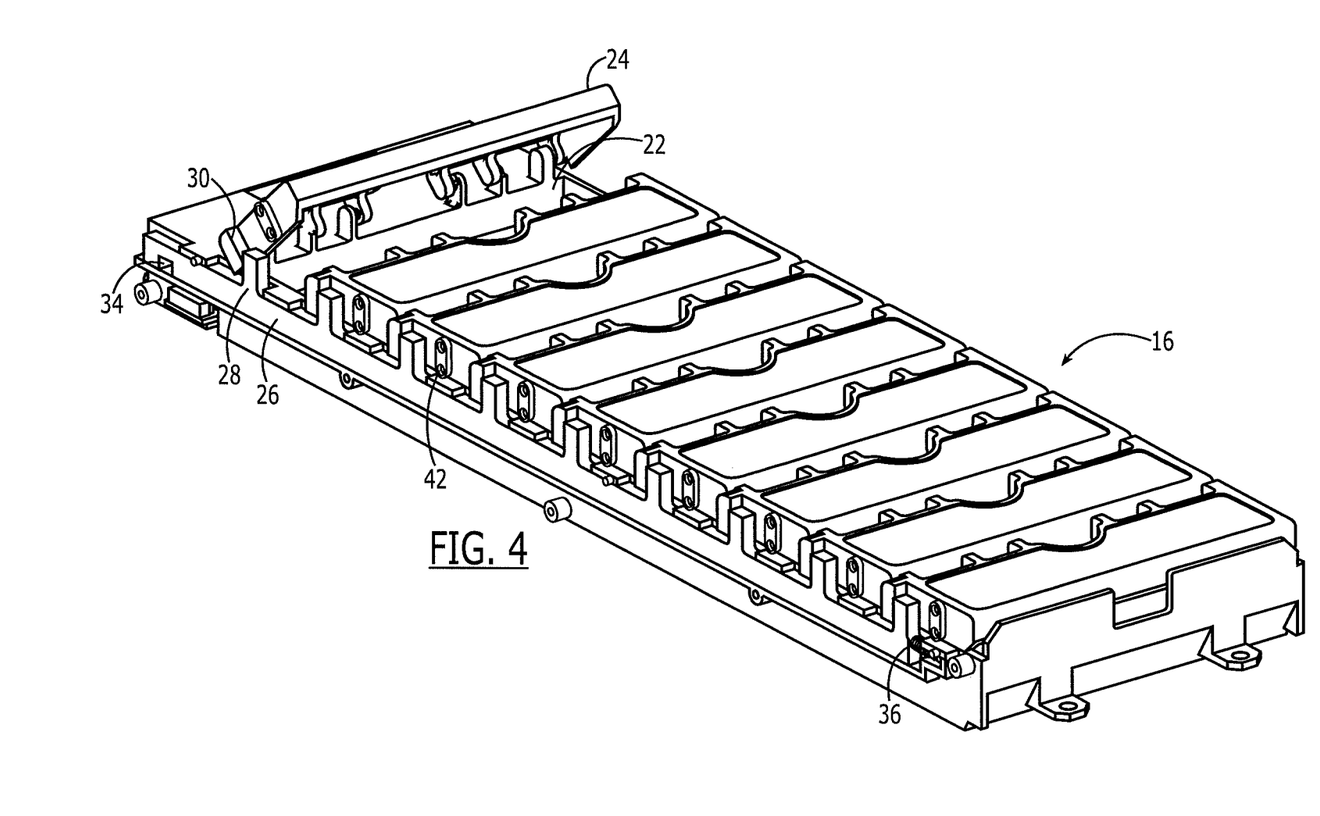
FIG. 4 is a perspective view of the portion of the drawer assembly of FIG. 3 in which one lid has been opened by about 45°.
Figure 6:
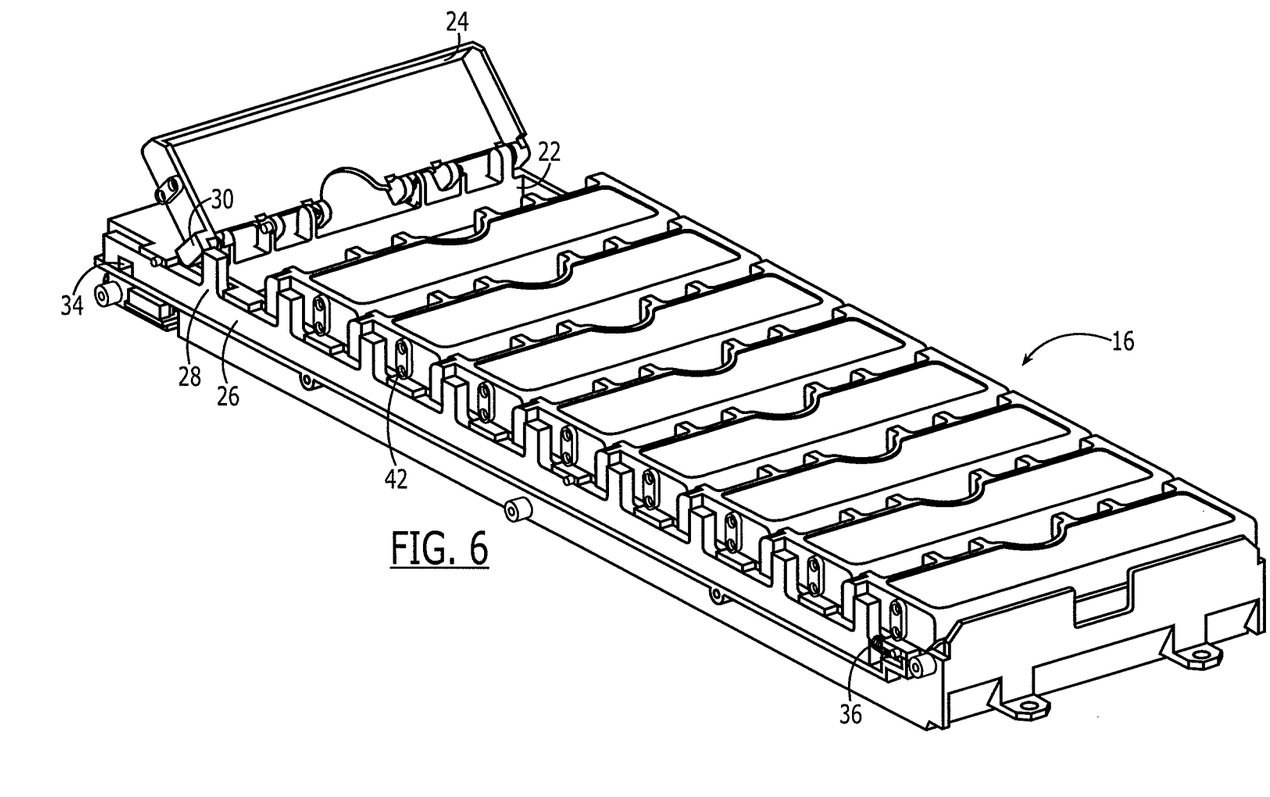
FIG. 6 is a perspective view of the portion of the drawer assembly of FIG. 3 in which one lid has been opened by about 135°.
Figure 7:
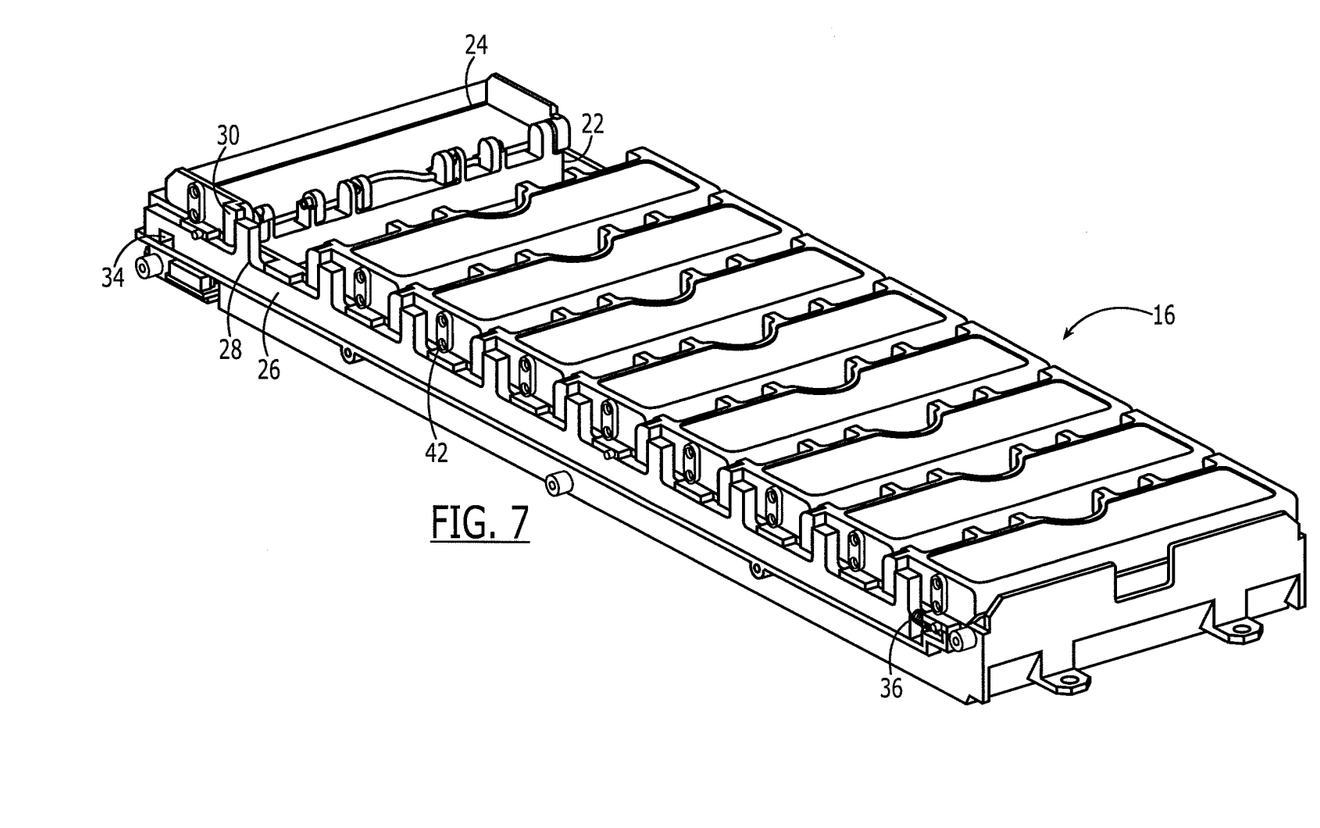
FIG. 7 is a perspective view of the portion of the drawer assembly of FIG. 3 in which one lid has been fully opened by about 180'.

Once the linkage member 26 has been unlocked, the medication within the first pocket 22, that is, the pocket closest to the front of the drawer 16, may be accessed in the scenario illustrated in FIG. 3 in which the lids 24 of each of the pockets were previously closed. A medical provider may then rotate the lid of the first pocket upwardly through the positions shown in FIGS. 4-6 until the lid is fully opened as shown in FIG. 7. As shown in FIG. 4 in which the lid has been opened by about 45°, the interaction between the engagement member 30 of the lid and the engagement member 28 of the linkage member has forced the linkage member to move in a lengthwise direction toward the rear of the drawer and to somewhat compress the bias member 36. The bias member continues, however, to apply a force that urges the linkage member toward the front of the drawer. As such, if the medical provider were to release the lid in the position shown in FIG. 4, or at any angle less than 90°, the bias member would return the linkage member to its nominal position as shown in FIG. 3 and would cause the lid to be closed.

Figure 5:
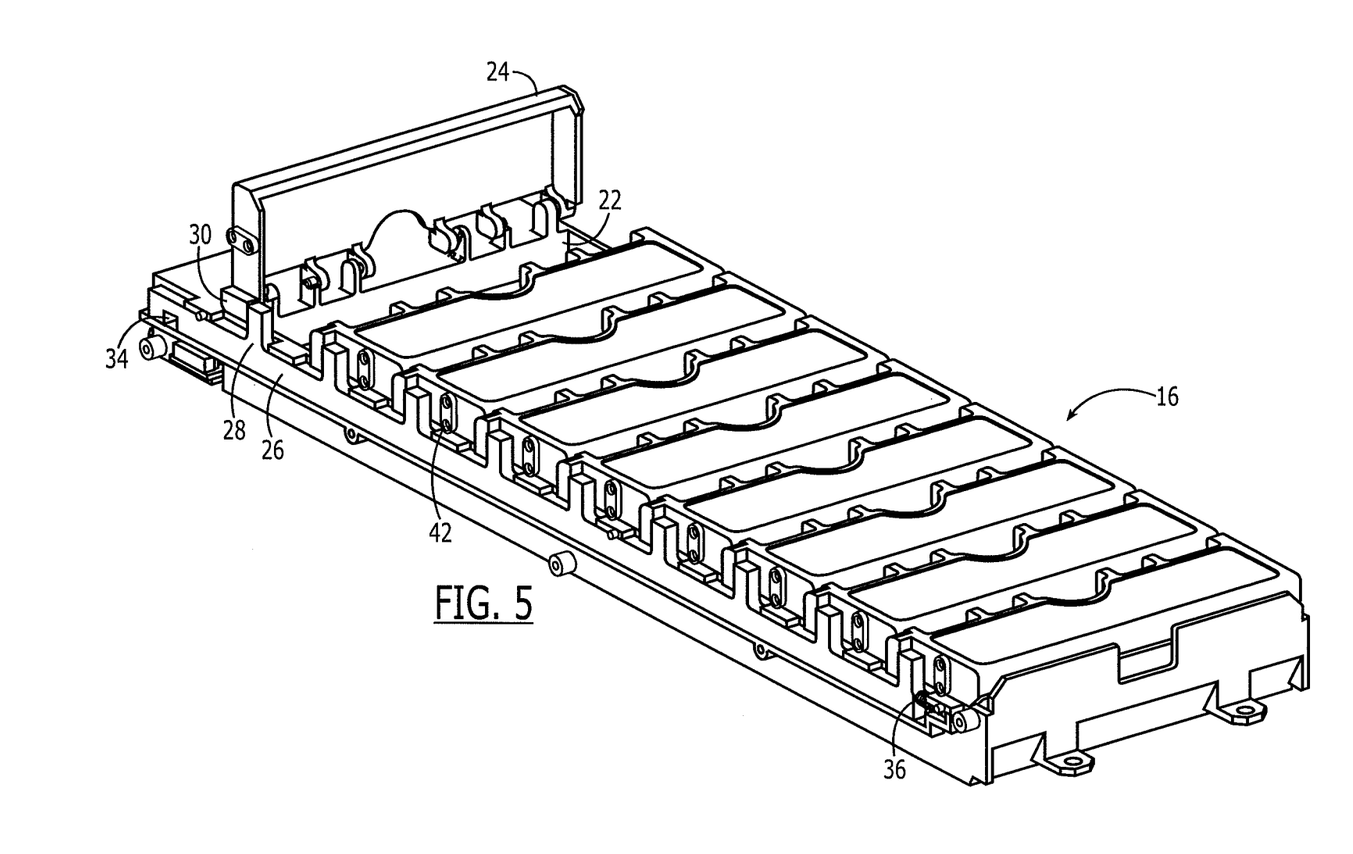
FIG. 5 is a perspective view of the portion of the drawer assembly of FIG. 3 in which one lid has been opened by about 90°.

As shown in FIG. 5, once the lid 24 has been opened 90°, the lid may be released and the lid will remain in the 90° position. As the lid is further opened, such as to an angle of 135° as shown in FIG. 6, the force applied by the bias member 36 to the linkage member 26 will urge the lid to a fully open position. Thus, if the medical provider were to release the lid in the position shown in FIG. 6 in which the lid is at an angle of 135° relative to the closed position or at any angle between 90° and 180°, the force applied by the bias member will move the linkage member forward relative to the plurality of pockets to the nominal position of the linkage member and will cause the lid to move to the fully open position at an angle of 180° relative to the closed position as shown in FIG. 7.

Once the lid 24 has been opened, such as to the fully opened position as shown in FIG. 7, the medical provider may access the medication within the pocket 22. In one embodiment, the lid will then remain in the fully opened position until the medication has been restocked or the pocket has otherwise been refilled, at which point in time the lid may again be closed, as described below. Once the lid for the first pocket closest to the front of the drawer 16 has been opened, the lid of the second pocket, that is, the pocket immediately rearward of the first pocket, may be opened while the linkage member 26 remains in the second state, e.g., the unlocked state, and the medication within the second pocket may then be accessed. If the medical provider is to retrieve the medication from a plurality of pockets, the pockets may be opened in a sequential fashion such as from the front to the rear of the drawer while the linkage member remains unlocked. However, the linkage member may by relocked once a lid, such as the lid of the first pocket, has been opened, as detected by a sensor as described below. In this regard, once a lid has been fully opened, the bias member may force the linkage member into its nominal position with the cut-out 34 aligned with the latch 32 and the latch may then be moved to the first position so as to re-engage the linkage member. For example, the computer may control the movement of the latch from the second unlocked position to the first locked position once the lid of the pocket has been opened, thereby preventing access to the medication within the other pockets, absent further authorization.

Thereafter, if the medical provider is again authorized to access medication from the drawer 16, the computer may cause the linkage member 26 to be unlocked, such as by causing the latch 32 to move from the first position to the second position. The pocket 22 closest to the front of the drawer 16 that is not currently in the open position may then be accessed by opening its lid 24 in the same manner as described above. In the embodiment illustrated in FIG. 7 in which the lid of the first pocket has been opened, the lid of the second pocket may next be opened to access the medication therein. The lids of the third pocket, the fourth pocket and so on may then be opened in a sequential manner, either while the linkage member remains in a second unlocked state or following repeated locking and unlocking of the linkage member by the latch.

In the illustrated embodiment, the drawer 16 may include a landing surface 36 proximate the front of the drawer for the lid 24 that otherwise covers the first pocket 22 to rest upon once fully opened, as shown in FIG. 7. However, the drawer need not necessarily include such a landing surface, but may be differently configured in other embodiments. As the lids of the other pockets are sequentially opened, the lids will generally cover the pocket immediately forward of the lid once the lid is in the fully open position. As a result of the sequential access of the pockets, however, the immediately forward pocket has already been accessed and the medication has already been removed therefrom such that the covering of the immediately forward pocket by the lid does not restrict any authorized access to the medication.

Figure 8:
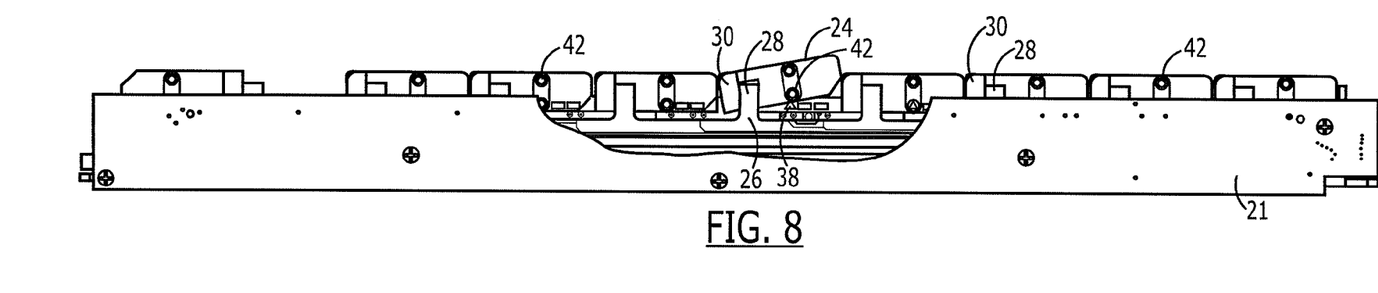
FIG. 8 is a fragmentary side view of a drawer assembly according to one embodiment of the present invention illustrating a relationship between a sensor and a magnet carried by a lid.

As indicated in the foregoing discussion, the pockets 22 may be positioned and the lids 24 may be configured so as to require the lids to be opened in a sequential fashion. As shown in the fragmentary side view of FIG. 8, the lids may be positioned relatively close to one another with little, if any, clearance between adjacent lids in a lengthwise direction. As such, even in an instance in which the linkage member 26 has been unlocked, the only lid that may be opened is the lid of the first pocket closest to the front of the drawer 16 in an instance in which no lid is already in the open position or the lid of the pocket adjacent to, e.g., immediately rearward of, an uncovered pocket in an instance in which one or more lids have been opened and remain in the open position. In other words, in an instance in which one or more lids proximate the front of the drawer have been opened and remain open, the lid of the first pocket from the front of the drawer that has a closed lid is the only lid that may be opened. As shown in FIG. 8, for example, any effort to open another lid that is not proximate the front of the drawer or an open pocket will be prevented by interfering mechanical contact with the lid covering the pocket immediately forward of the lid that efforts are being made to open. Thus, the drawer assembly of the illustrated embodiment is configured such that the lids must be opened in a sequential fashion, thereby further controlling access to the medications within the pockets of the drawer.

The drawer assembly of one embodiment is also configured to detect the movement of a lid 24 from a closed position to an open position, as well as from an open position to a closed position. Based upon the detection of the movement of the lid, the dispensation of medication within the pocket 22 may also be detected. While the opening or closing of a lid may be detected or sensed in various manners including, for example, optically by use of gap sensors, flags or the like, the drawer assembly of the illustrated embodiment includes a plurality of sensors 38 (represented by triangles in FIG. 8) carried by a panel 40 that is positioned so as to extend alongside the plurality of pockets. In the embodiment of FIG. 8 in which a portion of the side panels 21, 40 have been removed to show the alignment of the sensors (represented by triangles) with the lids. In this regard, a sensor is generally associated with and located adjacent to each lid. Correspondingly, each lid may include one or more magnets 42 that are carried by and move with the lid. In the illustrated embodiment, each lid may include a first magnet and a second magnet with the first magnet being positioned above the second magnet in an instance in which the lid is closed. In the closed position, the sensor associated with a respective lid may be aligned with the second magnet carried by the lid. As a result of this alignment, the sensor may detect the presence of the second magnet and may accordingly determine that the lid is closed. Upon opening or attempted opening of the lid, however, the second magnet is moved out of alignment with the respective sensor. The sensor may detect the displacement of the second magnet and may accordingly detect that the lid has been opened and the mediation within the respective pocket has been accessed. Once a lid has been fully opened, the first magnet may be aligned with a sensor which may detect that the lid has been moved 180°. The plurality of sensors may be in communication with the computer of an automated medication dispensing cabinet 10 and may report the status of the lids of the plurality of pockets including, for example, instances in which the lids have been opened or closed. As such, the computer may maintain a record, such as within memory, of the pockets that have been accessed and are considered empty and the pockets that have not been accessed and that still include medication.

Once all or at least a sufficient number or percentage of the pockets 22 have been accessed, the computer may direct that the medication within the cabinet 10 be replenished. In this regard, the drawer 16 may be accessed, such as by slidably extending the drawer from the cabinet body 12. Medication may then be placed within the open pocket and, after unlocking the linkage member 26, the lid 24 that covers the previously open pocket may be closed. Medication may then be placed in the next open pocket, and the lid for this pocket may also be closed. This process may be repeated, again in a sequential fashion, albeit in an opposite direction, that is, from the rear to the front of the drawer, from the direction in which the medication was accessed, until each of the pockets has been replenished. The drawer may then be returned to the closed position for further dispensing operations.

Although example embodiments of the drawer assembly have been described above, the drawer assembly may be differently configured in other embodiments. For example, the drawer assembly of one embodiment may include a plurality of linkage members 26, such as a plurality of linkage bars, that controllably lock and unlock different ones of the pockets 22. In this embodiment, the drawer assembly may include a first linkage bar extending along one side of the pockets and a second linkage bar extending along the other side of the pockets. The first linkage bar may engage the lids 24 of some of the pockets, while the second linkage bar may engage the lids of the remainder of the pockets. By way of example, the pockets may be designated as 1, 2, 3, 4, etc. with a lower numbered pocket being closer to the front of the drawer than a higher numbered pocket. As such, the first linkage bar of this embodiment may engage the lids of the odd numbered pockets, while the second linkage bar may engage the lids of the even numbered pockets. By including first and second linkage bars that engage the lids of the odd and even numbered pockets, respectively, a single pocket may be unlocked without permitting access to any other pocket that still contains medication. In an instance in which the lids of all of the pockets are closed, the first linkage bar may be unlatched, thereby permitting the lid of the first pocket to be opened and the medication within the first pocket to be accessed. By continuing to latch the second linkage bar, the second pocket and, in fact, all of the even numbered pockets remain locked in a closed position. Additionally, even though the first linkage bar is unlatched, access to the third pocket as well as all other odd numbered pockets is also restricted since the interference (or lack of clearance) between the lid of an odd numbered pocket and the lid of the pocket immediately forward of the odd numbered pocket prevents the lid of the odd numbered pocket from being opened. Thus, the first and second linkage bars of this embodiment may be alternatively latched and unlatched to provide access to a single pocket at any one time.

The drawer assembly of one embodiment is configured to provide controlled access of the medications within the medication dispensing cabinet 10, while permitting an authorized medical provider to access the medications in a quick and efficient manner. Additionally, the medication dispensing cabinet and associated drawer assembly of an embodiment of the present invention permits a record to be maintained of the medications that have been dispensed and the medications that remain within the medication dispensing cabinet, such as in an automated manner, to thereby facilitate dispensing of the medications and subsequent replenishment of the medications within the medication dispensing cabinet.

Figure 9:
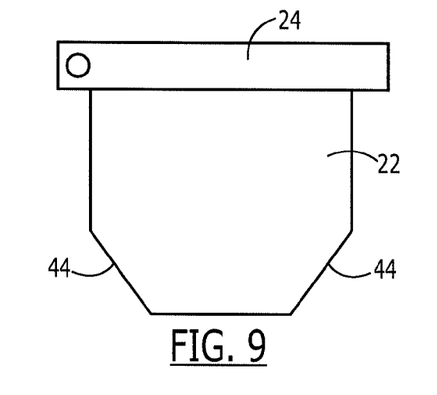
FIG. 9 is a side view of a pocket within a drawer assembly according to one embodiment of the present invention.

In order to facilitate retrieval of the medication from a pocket 22 having a lid 24 that has been moved to the open position, a pocket may be configured to have at least one and, in one embodiment, a pair of opposed inclined side surfaces 44, such as shown in the side view of FIG. 9. In this embodiment, the inclined or inwardly tapered side surfaces facilitate a medical provider grasping medication, such as in the form of a tablet, a pill or the like, within a lower portion of the pocket. As such, the medical provider will not only be able to efficiently open a lid of the pocket in which the medication is disposed, but may also efficiently retrieve the medication from the pocket in accordance with an embodiment of the present invention.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A medication dispensing cabinet comprising:
    a cabinet body;
    a plurality of drawers disposed within and configured for slidable extension relative to the cabinet body;
    a plurality of pockets serially positioned within a first drawer, each pocket including a lid configured to cover the pocket and limit access to medication within the pocket; and
    a linkage member configured to operably engage the lids of the plurality of pockets, wherein the linkage member has a first state in which the linkage member prevents one or more of the lids from being opened and a second state in which the linkage member permits a lid to be opened in accordance with a predefined sequential order,
    wherein the pockets are positioned and the lids are configured such that a second lid is prevented from fully opening as a result of operable contact with a first lid of an adjacent pocket in an instance in which the first lid of the adjacent pocket has not yet been opened.

2. A medication dispensing cabinet according to claim 1 further comprising a latch configured to engage the linkage member in the first state and to be disengaged from the linkage member in the second state.

3. A medication dispensing cabinet according to claim 1 further comprising a bias member configured to urge the linkage member into operable engagement with the lids of the plurality of pockets.

4. A medication dispensing cabinet according to claim 1 wherein each lid comprises an engagement member extending laterally therefrom, and wherein the linkage member comprises a plurality of engagement members spaced lengthwise therealong for operable engagement with the engagement members of respective lids.

5. A medication dispensing cabinet according to claim 3 wherein the bias member is configured to urge the linkage member into operable engagement with the lids of the pockets such that the lids are biased to a closed position in an instance in which the lids are opened by no more than a first predetermined amount and are biased to an open position in an instance in which the lids are opened by at least a second predetermined amount.

6. A medication dispensing cabinet according to claim 1 wherein the lids are configured to move between a closed position and an open position that are separated by 180°.

7. A medication dispensing cabinet according to claim 1 further comprising a sensor configured to detect opening or closing of a lid.

8. A medication dispensing cabinet according to claim 7 further comprising one or more magnets carried by each lid, wherein the sensor is configured to detect at least one of the magnets in an instance in which a respective lid is opened or closed.

9. A medication dispensing cabinet according to claim 4 wherein each lid and the linkage member are configured such that operable engagement of respective engagement members of the lids by the plurality of engagement members of the linkage member serves to alternately maintain the lids in each of at least two different positions.

10. A medication dispensing drawer assembly comprising:
a drawer;
a plurality of pockets serially positioned within the drawer, each pocket including a lid configured to cover the pocket and limit access to medication within the pocket; and
a linkage member extending alongside the plurality of pockets and configured to operably engage the lids of the plurality of pockets, wherein the linkage member has a locked state in which the linkage member prevents one or more of the lids from being opened and an unlocked state in which the linkage member permits a lid to be opened in accordance with a predefined sequential order,
wherein the pockets are positioned and the lids are configured such that a second lid is prevented from fully opening as a result of operable contact with a first lid of an adjacent pocket in an instance in which the first lid of the adjacent pocket has not yet been opened.

11. A medication dispensing drawer assembly according to claim 10 further comprising a latch configured to engage the linkage member in the locked state and to be disengaged from the linkage member in the unlocked state.

12. A medication dispensing drawer assembly according to claim 10 further comprising a bias member configured to urge the linkage member into operable engagement with the lids of the plurality of pockets.

13. A medication dispensing drawer assembly according to claim 12 wherein the bias member is configured to urge the linkage member into operable engagement with the lids of the pockets such that the lids are biased to a closed position in an instance in which the lids are opened by no more than a first predetermined amount and are biased to an open position in an instance in which the lids are opened by at least a second predetermined amount.

14. A medication dispensing drawer assembly according to claim 10 wherein the lids are configured to move between a closed position and an open position that are separated by 180°.

15. A medication dispensing drawer assembly according to claim 10 wherein each pocket includes at least one inclined side surface.

16. A medication dispensing drawer assembly according to claim 10 further comprising a sensor configured to detect opening or closing of a lid.

17. A medication dispensing drawer assembly according to claim 16 further comprising one or more magnets carried by each lid, wherein the sensor is configured to detect at least one of the magnets in an instance in which a respective lid is opened or closed.

18. A medication dispensing drawer assembly according to claim 10 wherein each lid comprises an engagement member extending laterally therefrom, and wherein the linkage member comprises a plurality of engagement members spaced lengthwise therealong for operable engagement with the engagement members of respective lids.

19. A method for controllably dispensing medication comprising:
maintaining a linkage bar in a locked state in order to prevent one or more lids that cover respective pockets within a drawer from being opened;
unlocking the linkage bar;
permitting a lid to be opened in accordance with a predefined sequential order while the linkage bar is unlocked to permit access to medication within the respective pocket; and
relocking the linkage bar while the lid remains open,
wherein permitting a lid to be opened comprises preventing a second lid of a pocket from fully opening as a result of operable contact with a first lid of an adjacent pocket in an instance in which the first lid of the adjacent pocket has not yet been opened due to positioning of the pockets and configuration of the lids.

20. A method according to claim 19 further comprising sensing the opening or closing of the lid.

\* \* \* \* \*